United States Patent
Tsutsui et al.

(10) Patent No.: US 6,885,448 B2
(45) Date of Patent: Apr. 26, 2005

(54) PHOTON CORRELATOR

(75) Inventors: Kazunori Tsutsui, Osaka (JP); Motonobu Akagi, Shiga (JP); Yasushi Zasu, Kyoto (JP); Katsuhiro Morisawa, Kyoto (JP)

(73) Assignee: Otsuka Electronics Co., Ltd., Osaka (JP)

(*) Notice: Subject to any disclaimer, the term of this patent is extended or adjusted under 35 U.S.C. 154(b) by 163 days.

(21) Appl. No.: 10/276,994
(22) PCT Filed: Mar. 26, 2002
(86) PCT No.: PCT/JP02/02882
§ 371 (c)(1), (2), (4) Date: Nov. 20, 2002
(87) PCT Pub. No.: WO02/082028
PCT Pub. Date: Oct. 17, 2002

(65) Prior Publication Data
US 2003/0133110 A1 Jul. 17, 2003

(30) Foreign Application Priority Data
Mar. 30, 2001 (JP) .................................. 2001-101086

(51) Int. Cl.⁷ .............................................. G01N 15/02
(52) U.S. Cl. .................... 356/336; 356/338; 356/341; 356/343; 250/336.1
(58) Field of Search ................................ 356/335–343; 250/574, 336.1, 213 VT, 227.11, 227.16

(56) References Cited

U.S. PATENT DOCUMENTS

| | | | | |
|---|---|---|---|---|
| 4,346,991 A | * | 8/1982 | Gardner et al. | 356/28.5 |
| 4,975,237 A | * | 12/1990 | Watling | 356/338 |
| 5,015,094 A | * | 5/1991 | Oka et al. | 356/336 |
| 5,124,551 A | * | 6/1992 | Urakami et al. | 250/336.1 |
| 5,155,549 A | * | 10/1992 | Dhadwal | 356/336 |
| 5,907,399 A | * | 5/1999 | Shirasawa et al. | 356/336 |

FOREIGN PATENT DOCUMENTS

| | | |
|---|---|---|
| JP | 2-96636 | 4/1990 |
| JP | 4-181127 | 6/1992 |

* cited by examiner

Primary Examiner—Frank G. Font
Assistant Examiner—Sang Hoang Nguyen
(74) Attorney, Agent, or Firm—Finnegan, Henderson, Farabow, Garrett & Dunner LLP

(57) ABSTRACT

A photon correlator comprises a plurality of sampling gates $11a$–$11e$ which are open during different periods of time; a plurality of memories $12a$–$12e$ each provided corresponding to each of the plurality of sampling gates $11a$–$11e$ for storing data corresponding to the number of photons; and a data processing control section for reading out the data stored in the memories $12a$–$12e$, and performing a correlation calculation by means of software. The mechanism of the hardware comprising the sampling gates $11a$–$11e$ and memories $12a$–$12e$ enables high-speed writing of data in the memories and real-time read out of the data. In addition, the software performs correlation calculations in parallel with the above processing. Accordingly, the particle sizes and diffusion coefficient of particles in a fluid can be obtained at high speed under various conditions.

1 Claim, 5 Drawing Sheets

PHOTON CORRELATOR

TECHNICAL FIELD

The present invention relates to a photon correlator for measuring scattering light (hereinafter referred to as "photon") that is scattered in a pattern of pulses from particles in a fluid when the particles are irradiated with light in phase such as a laser beam.

BACKGROUND ART

For quantitative and statistical data processing on time distribution of photons, a photon correlator counts the number of photons incident on the detector during a time when the sampling gate is open (hereinafter referred to as "sampling time"), and the number of photons incident on the detector during a sampling time which is a time τ later than the previous sampling time, thereby calculating an autocorrelation coefficient.

FIG. 5 illustrates a method of counting the number of photons in which the horizontal axis indicates time t. A sampling time is indicated by ts. The number of photons detected within the sampling time at a time t is indicated by N (t), and the number of photons detected within the sampling time at a time (t+τ) is indicated by N(t+τ). The autocorrelation coefficient G(t) can be obtained by calculating the product of N(t) and N(t+τ), and then integrating with respect to time t. Generally, the above mentioned correlation time τ is in an extremely wide range from several microseconds to several dozen milliseconds.

For such autocorrelation coefficient calculation, either a photon correlator utilizing hardware or a photon correlator utilizing software has conventionally been used.

A photon correlator utilizing hardware has a mechanism for counting the number photons mentioned above, and a multiplier for cumulative multiplication, which is realized in a shift register or the like, for performing autocorrelation calculation based on the counted number of photons, and is characterized in that it is capable of performing high-speed, real-time correlation calculations.

On the other hand, a photon correlator utilizing software performs data processing by storing the number photons sampled in the memory, and reading out the count data that have been stored in the memory in accordance with a program. Accordingly, the sampling time and data processing method can be set and modified flexibly.

In the above-mentioned photon correlator utilizing hardware, the parameters for autocorrelation calculation including the sampling time ts, the available range of correlation time τ, the increment with which the correlation time τ is extended within the range, and the normalization method are preliminarily fixed. Accordingly, flexible data processing such as increasing the resolution during a correlation time in a specific range is impossible. In addition, it is also impossible to remove abruptly detected data of scattering light caused by dust in the sample.

On the other hand, the photon correlator utilizing software takes longer processing time than the photon correlator utilizing hardware. When a great deal of photon data are loaded to obtain a long correlation time, processing of the data takes such a long time that the photon measurement is suspended during the period, causing the problem of poor data loading efficiency.

It is therefore an object of the present invention to provide a photon correlator having both the high-speed of hardware processing and the flexibility of software processing.

SUMMARY OF THE INVENTION

A photon correlator according to the present invention comprises: a plurality of sampling gates which are open during different periods of time; a plurality of memories each provided corresponding to each of the plurality of sampling gates for storing data corresponding to the number of photons; and a data processing control section for reading out the data stored in the memories in parallel with storing of the data in the memories, and performing a correlation calculation by means of software. The sampling gates open their respective gates not at random timings, but in synchronous timing.

In the above structure, the mechanism of the hardware comprising the sampling gates and memories enables high-speed writing of data in the memories and real-time read out of the data. In addition, the software performs correlation calculations in parallel with the above processing. Accordingly, data including the particle sizes and diffusion coefficient of particles in a fluid can be obtained at high speed under various conditions.

Furthermore, since correlation calculations are performed by the software during and in parallel with the measurements, data abnormalities due to dust in the sample can be easily detected, facilitating removal of the abnormal data.

In order to avoid prolongation of data processing time, the data processing control section preferably selects a memory (memories) from which data are read out among the plurality of memories in accordance with the correlation time τ.

The data processing control section preferably includes an outside memory to be utilized for correlation calculations, and the outside memory preferably stores data of the number of photons. By utilizing the outside memory, a corresponding number of data of the number of photons can be stored so that correlation calculation can be performed even when the correlation time τ for a correlation calculation is extended. The "corresponding number" mentioned above is the number of photons detectable during a time when photons are taken in. For example, when the number of photons being scattered is 10.000 per second, the number of photons detected for 2 seconds is 20.000.

A preferred embodiment of the present invention will be hereinafter described referring to the appended drawings.

BEST MODE FOR CARRYING OUT THE INVENTION

Figure 1:
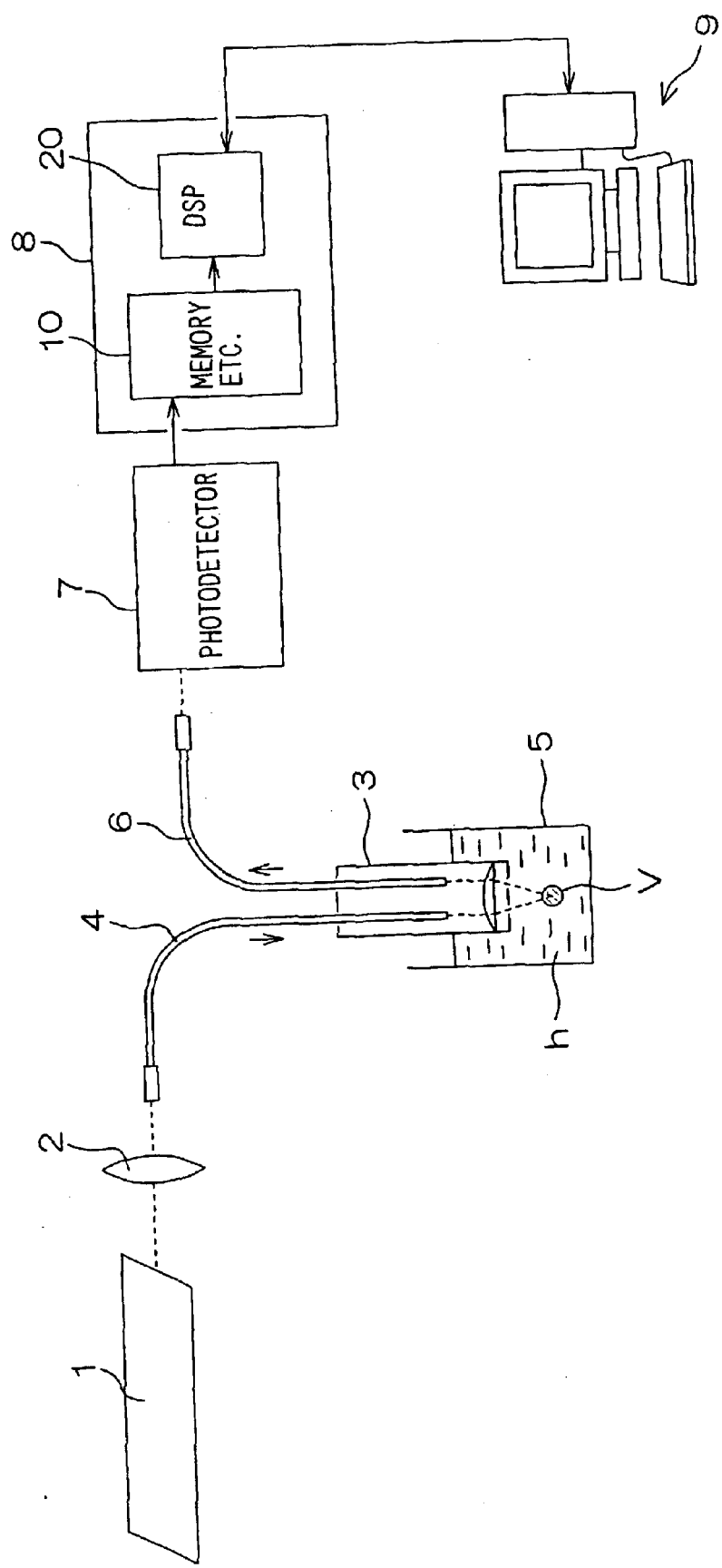
FIG. 1 shows the overall configuration of a measuring system including a photon correlator 8 according to this invention.

FIG. 1 shows the overall configuration of a measuring system including a photon correlator 8. Coherent light launched from laser equipment 1 is converged by a lens 2 to enter a light input optical fiber 4. An end of the light input optical fiber 4 is connected to a probe 3 for measuring light scattering. The probe 3 for measuring light scattering is inserted into a cell 5 that is filled with a sample fluid h so that the sample fluid h is illuminated with a laser beam emitted from the end of the probe 3 for measuring light scattering.

Light scattered from a scattering volume V in the sample enters a scattered light measuring optical fiber 6 provided in the probe 3 for measuring light scattering and is received by a photodetector 7 such as a photomultiplier, where time series data of photons are measured. The autocorrelation coefficients of the data are calculated at the photon correlator 8. A host computer for calculating the particle sizes and diffusion coefficient and the like of particles in the fluid is denoted by the numeral 9. The host computer 9 performs overall control of the measuring system.

Incidentally, the light input optical fiber 4 and the scattered light measuring optical fiber 6 are preferably single-mode optical fibers in view of maintaining the coherence of light.

The photon correlator 8 has the function 10 to count the number of photons and the function 20 to perform autocorrelation calculations. The function 10 to count the number of photons is realized by hardware comprising gate circuits and memories. The function 20 to perform autocorrelation calculations is realized by a built-in computer (this computer is hereinafter referred to as "DSP (Digital Signal Processor)") when it executes a program recorded in a recording medium such as a program ROM.

Figure 2:
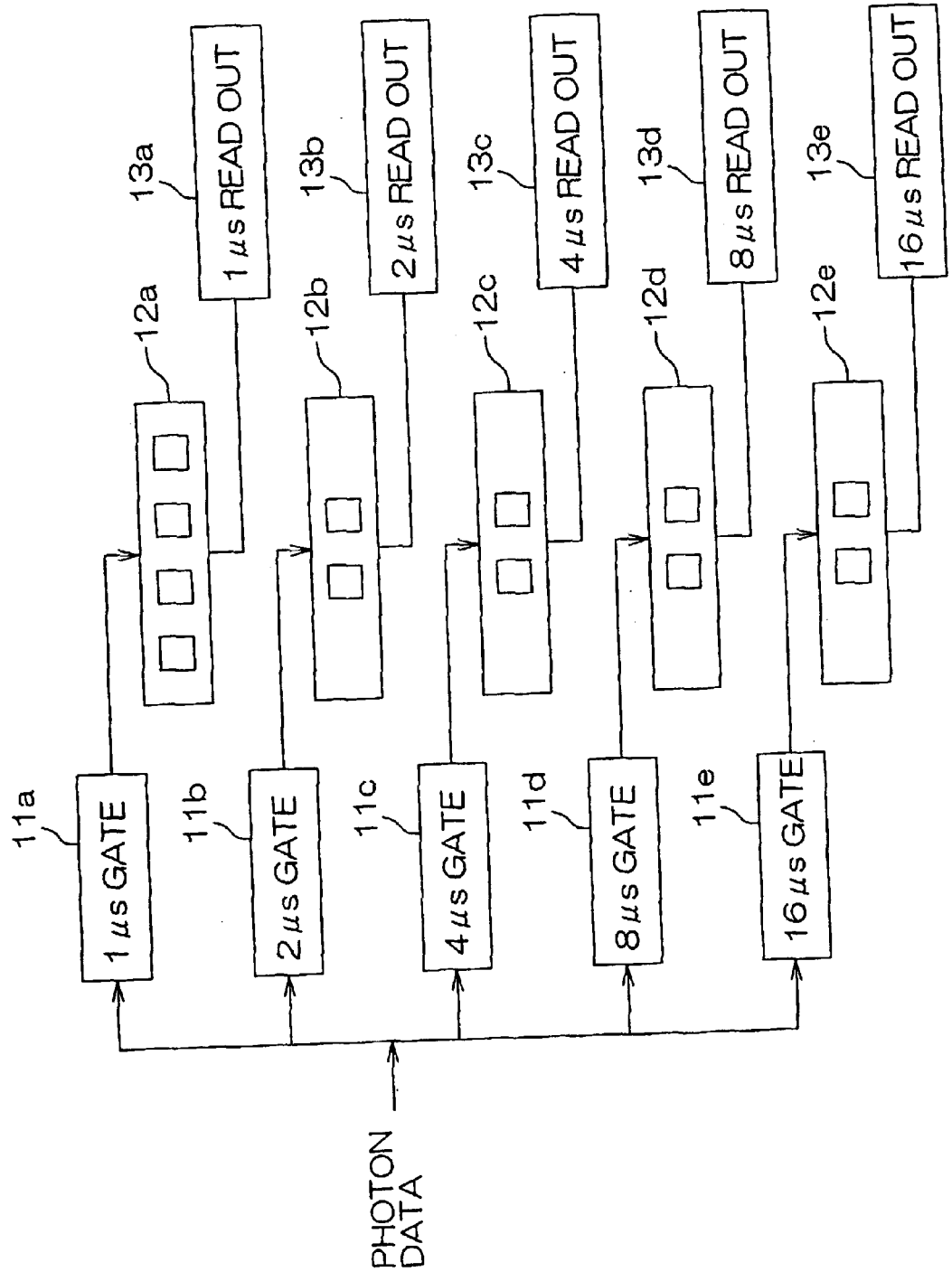
FIG. 2 shows the structure of hardware including gates and memories that realizes a function 10 to count the number of photons.

FIG. 2 illustrates the structure of the hardware comprising the gates and memories that realizes the function 10 to count the number of photons. Photon data, (these are, for instance, represented by pulsed voltages corresponding to the number of photons) outputted from the photodetector 7 are inputted into a plurality of gate circuits 11a–11e. The gate circuits 11a–11e open their respective gates synchronously with one another for different periods of time. In FIG. 2, there are five gate circuits 11a, 11b, 11c, 11d and 11e whose gates are open for 1 $\mu$sec, 2 $\mu$sec, 4 $\mu$sec, 8 $\mu$sec and 16 $\mu$sec, respectively.

The outputs from the gate circuits 11a–11e are given to memories 12a–12e, which are high-speed memories such as SRAMs that store the number photons. The memory 12a corresponds to the 1 $\mu$sec gate circuit 11a, and has four areas for storing data of the number photons. The memory 12a stores the data of the number of photons in these four areas in sequence. As will be described later, data are sequentially read out before the four areas become full. Accordingly, the memory 12a can keep storing a series of data of the number photons.

The memory 12b corresponds to the 2 $\mu$sec gate circuit 11b, and has two areas for storing data of the number photons. The memory 12b stores data of the number photons sequentially in these two areas. As will be described later, data are sequentially read out before the two areas become full. Accordingly, the memory 12b can keep storing a series of data of the number photons.

The memory 12c corresponds to the 4 $\mu$sec gate circuit 11c, and has two areas for storing data of the number photons. The memory 12d corresponds to the 8 $\mu$sec gate circuit 11d, and has two areas for storing data of the number photons. The memory 12e corresponds to the 16 $\mu$sec gate circuit 11e, and has two areas for storing data of the number photons. These areas are used in the same way as described referring to the memory 12b.

The reason for collecting time series data during different periods of time ranging from 1 $\mu$sec to 16 $\mu$sec is that it is desired to select time series data during the optimal period of time in accordance with the correlation time $\tau$ for a correlation calculation.

For example, when performing all the calculations with data during the 1 $\mu$sec periods is attempted, the longer the correlation time $\tau$ becomes, the greater the number of data becomes, resulting in a prolonged data processing time. By selectively using time series data during different periods of time, such increase in data processing time can be avoided.

For example, for a correlation calculation with a correlation time $\tau$ of 1–20 $\mu$sec, time Series data during the 1 $\mu$sec periods are optimal. For a correlation calculation with a correlation time $\tau$ of 20–80 $\mu$sec, time series data during the 2 $\mu$sec periods are used. For a correlation calculation with a correlation time $\tau$ of 480–960 $\mu$sec or more, time series data during the 16 $\mu$sec periods are used. For a correlation time $\tau$ longer than these, time series data during the 16 $\mu$sec periods are thinned to be used. However, the above-mentioned numbers are only an example, and in practice, an optimal combination of numbers is determined according to the sample and the quantity of the scattering light.

There are also provided read-out circuits 13a–13e. The read-out circuit 13a reads out data of the number of photons stored in the memory 12a sequentially or alternately with a delay of a certain period, which is a very short time e.g. several times smaller than 1 $\mu$sec, after the data of the number of photons are written in the memory. In the same way, each of the read-out circuits 13b–13e reads out data alternately with a delay of a certain period (e.g. several times smaller than 1 $\mu$sec) after the data are written.

In the structure of the hardware described above, data of the number of photons during every 1 $\mu$sec are outputted from the read-out circuit 13a almost in real time. Data of the number of photons during every 2 $\mu$sec are outputted from the read-out circuit 13b almost in real time, and data of the number of photons during every 4 $\mu$sec are outputted from the read-out circuit 13c almost in real time. Data of the number of photons during every 8 $\mu$sec are outputted from the read-out circuit 11d almost in real time, and data of the number of photons during every 16 $\mu$sec are outputted from the read-out circuit 13e almost in real time.

Figure 3:
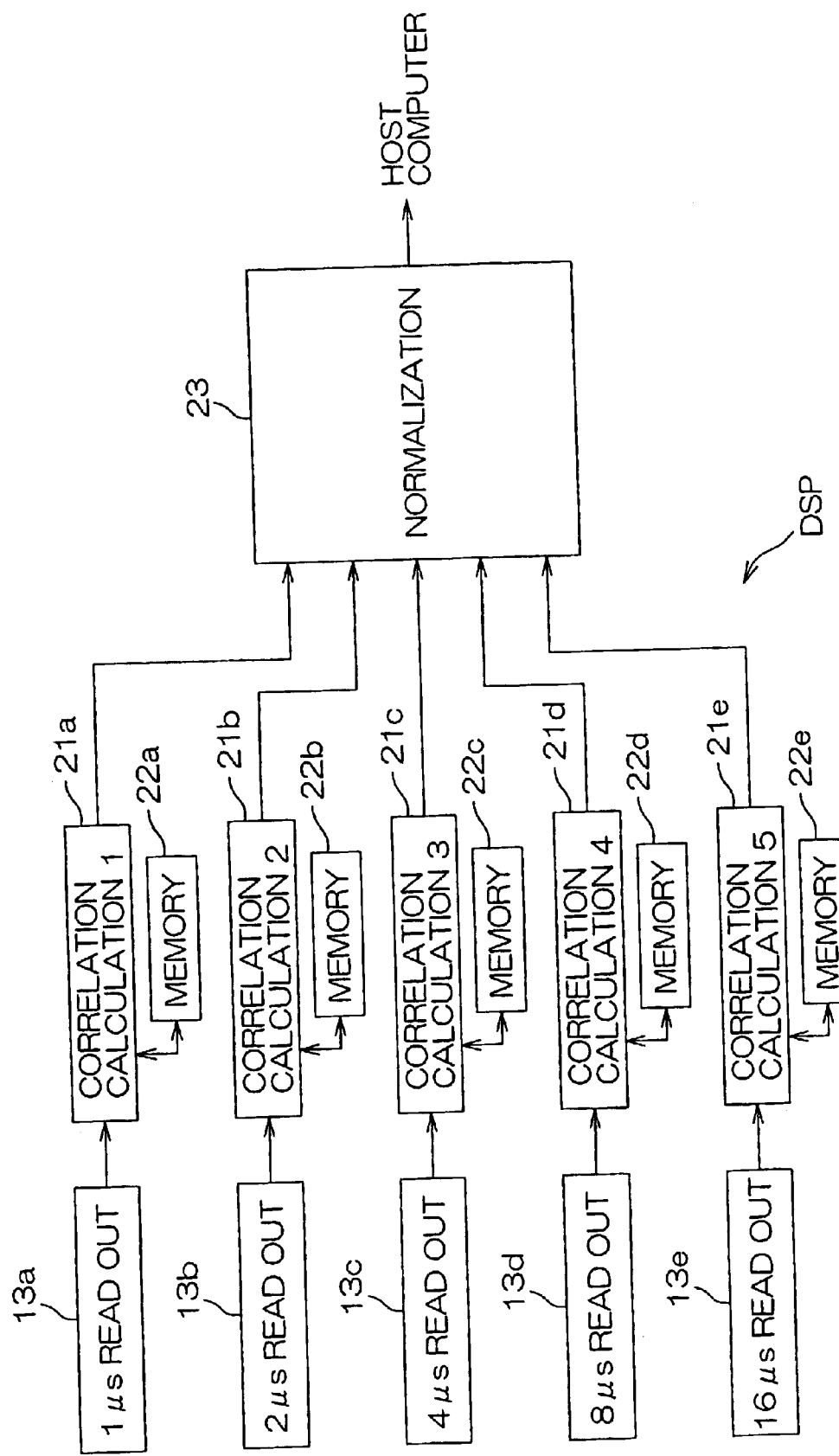
FIG. 3 is a block diagram illustrating a function 20 of DSP to perform autocorrelation calculations.

FIG. 3 is a block diagram illustrating the function 20 of DSP to perform autocorrelation calculations. Data of the number of photons from the read-out circuits 13a–13e are given to correlation calculation sections 21a–21e, respectively, where the data of the number of photons are stored in outside memories 22a–22e, each of which comprises a high-speed memory such as DRAM, SRAM or the like, and correlation calculations are performed using the data stored in the outside memories 22a–22e. The results are given to a normalization section 23, where normalization calculation is performed.

Figure 4:
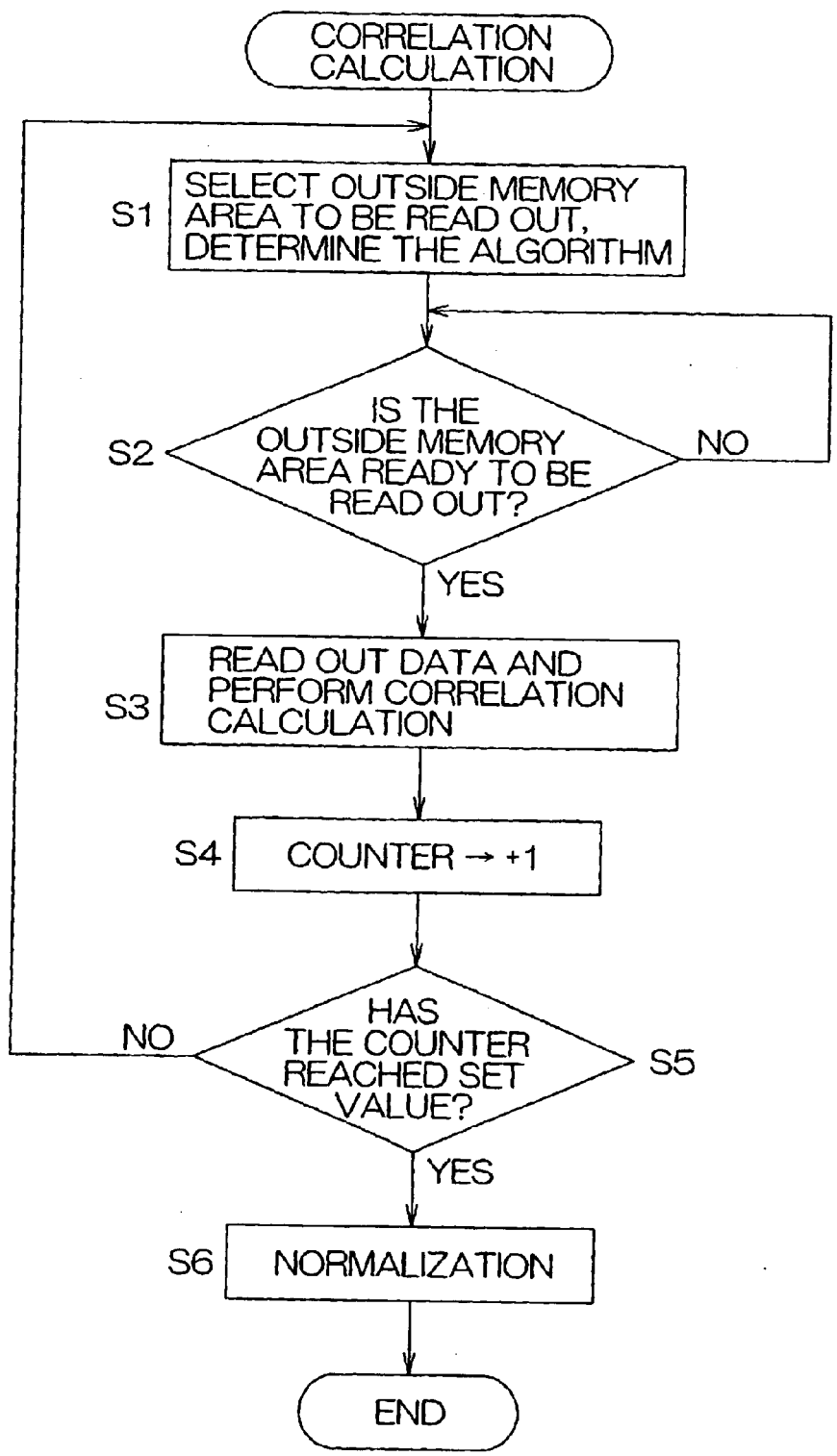
FIG. 4 is a flowchart illustrating a procedure of a correlation calculation performed at correlation calculation sections 21a–21e.
Figure 5:
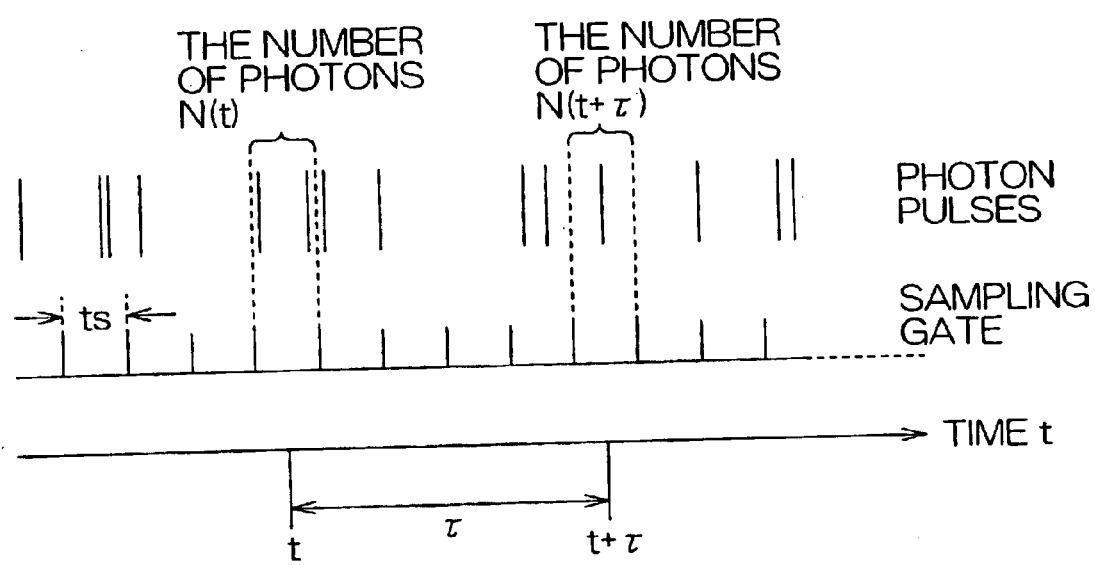
FIG. 5 illustrates a method of counting the number of photons.

FIG. 4 is a flowchart illustrating the procedure of a correlation calculation performed at the correlation calculation sections 21a–21e. To explain each step along the flowchart, first, DSP selects an outside memory to be read out from among 22a–22e, thereby identifying the kind of data (through which $\mu$sec gate the data are collected), and determines the algorithm including what correlation time $\tau$ is used and what range is used for the integration range (the number of data) (Step S1). DSP carries out these selection and determination in accordance with commands from the host computer 9.

Thereafter, whether the outside memory (22a–22e) is ready to be read out (that is, whether the necessary number of data have been stored) is judged (Step S2). When it is ready to be read out, the data are read out and a correlation calculation is performed (Step S3).

Now, the algorithm of the correlation calculation is described. For discrete representation, symbols, subscripts, superscripts and the like are changed in the following description from those used so far. The number of data is represented by M, sampling time points are indicated by j (j=1, 2, . . . , M), and correlation time is represented by k. The number of photons at the sampling time point j is represented by $n_j$.

An autocorrelation function $G_k$ is calculated as follows:

$$G_k = (1/M) \Sigma n_j\, n_{j-k} \text{ (j is from 1 to M)} \quad (1)$$

On completion of the correlation calculation, the counter is augmented by 1 (Step S4), and whether the counter has reached a set value is judged (Step S5). This set value corresponds to the number of times the correlation calculation is desired to be performed with the timing being delayed each time.

When the set value has been reached, the autocorrelation function is normalized (Step S6). The normalized autocorrelation function is indicated by $g_k$. $g_k$ is represented by the following equation:

$$g_k = G_k/S_0^2 \text{ (standard normalization)} \quad (2)$$

or $$g_k = G_k/S_0 S_k \text{ (symmetric normalization)} \quad (3)$$

where $S_k = \Sigma n_j$ (j is from 1-k to M-k), which is the average quantity of light.

Data of autocorrelation function obtained through the above process are sent to the host computer 9, where the particle size distribution, the diffusion coefficient of the particles and the like are calculated in accordance with a publicly known program.

A preferred embodiment of the present invention has been described so far. However, it is to be understood that this invention is not limited to this specific mode. For example, although in the embodiment shown in FIG. 2, the memory 12a comprises four memories and each of the memories 12b–12e comprises two memories, the number of memories is not limited to the numbers above. Also, various other modifications are possible within the scope of the present invention.

What is claimed is:

1. A photon correlator comprising:

a plurality of sampling gates which are open during different periods of time;

a plurality of memories each provided corresponding to each of the plurality of sampling gates for storing data corresponding to the number of photons;

a data processing control section for selecting a memory from which data are read out from among the plurality of memories in accordance with a correlation time τ, reading out the data stored in the selected memory, and performing a correlation calculation by means of software; and an outside memory provided separately from the plurality of memories that stores data of the number of photons, wherein read-out of data from the memories is performed in parallel with storing of data in the memories, and the data processing control section utilizes the outside memory to perform a correlation calculation by means of software.

* * * * *